United States Patent [19]

Migdal et al.

[11] Patent Number: 5,066,412
[45] Date of Patent: Nov. 19, 1991

[54] FRICTION MODIFIER ADDITIVE AND LUBRICATING OIL COMPOSITION CONTAINING SAME

[75] Inventors: Cyril A. Migdal, Croton-On-Hudson; Shailaja M. Shirodkar, Wappingers Falls, both of N.Y.; Thomas F. DeRosa, Passaic, N.J.; Edward F. Miller, Wappingers Falls, N.Y.

[73] Assignee: Texaco Inc., White Plains, N.Y.

[21] Appl. No.: 649,504

[22] Filed: Feb. 1, 1991

[51] Int. Cl.$^5$ ............................................. C10M 131/12
[52] U.S. Cl. ...................................... 252/54.6; 44/390
[58] Field of Search .......................... 252/54.6; 44/390

[56] References Cited

U.S. PATENT DOCUMENTS

| | | | |
|---|---|---|---|
| 3,081,342 | 3/1963 | Ver Nooy | 252/54.6 |
| 3,096,363 | 7/1963 | Ballard et al. | 252/54.6 |
| 3,752,847 | 8/1973 | Fletcher et al. | 252/54.6 |
| 4,394,134 | 7/1983 | Rowe | 252/54.6 |

*Primary Examiner*—Jacqueline V. Howard
*Attorney, Agent, or Firm*—Robert A. Kulason; James J. O'Loughlin; Vincent A. Mallare

[57] ABSTRACT

A polymeric lubricating oil additive containing pendant perfluoroaliphatic ester groups that behave as a fuel economy enhancer when added to lubricating oil compositions. The additive is prepared by the process which comprises reacting a perfluoroaliphatic alcohol with an alkenyl succinic acid anhydride to form a alakenyl succinic mono and/or diester in the presence of an acid catalyst.

7 Claims, No Drawings

FRICTION MODIFIER ADDITIVE AND LUBRICATING OIL COMPOSITION CONTAINING SAME

BACKGROUND OF THE INVENTION

This invention relates to a lubricant additive acting as a friction modifier, and, more particularly, to a process for producing an additive which imparts enhanced fuel economy when employed in a lubricating oil composition.

The addition of oligomeric waxes or oils of polytetrafluoroethylene (PTFE) to lubricating oils is designed to reduce wear and friction on mechanized components of internal combustion engines. Less frequent replacement of worn or damaged engine components and greater gasoline efficiency are direct consequences. PTFE oils or waxes are not, however, soluble in any known lubricating oil.

Thus, it is an object of the present invention to provide a lubricating oil composition and manufacturing process for it which has enhanced fuel economy. The lubricating oil composition consists of a major portion of a lubrication oil and a minor amount of a reaction product described herein. It is prepared by the process which comprises reacting a perfluoroaliphatic alcohol with an alkenyl succinic acid anhydride to form an alkenyl succinic mono and/or diester in the presence of an acid catalyst. This invention is significant in light of the need to reduce the fuel consumed by motor vehicles in order to protect our environment and conserve our natural resources.

U.S. Pat. No. 3,933,656 discloses a method of friction reduction between metal surfaces using a dispersion of polytetrafluoroethylene in lubricating oil.

U.S. Pat. No. 4,224,173 discloses a method of using polytetrafluoroethylene dispersions in lubricating oils to reduce friction and enhance fuel economy in internal combustion engines.

U.S. Pat. No. 4,284,518 discloses a method of using a colloidal dispersion of polytetrafluoroethylene as a wear resistant additive and fuel economizer during physical operation.

U.S. Pat. Application Ser. No. 07/434,611 discloses a polymeric lubricating oil additive containing pendant perfluoroaliphatic urethane units that behaves as a VI Improver and a fuel economy enhancer when added to lubricating oil compositions. The polymeric substrate may be a copolymer of 15-85 mole% ethylene and propylene or a terpolymer of 15-85 mole% ethylene, propylene, and 2-8- mole% of a non-conjugated diene or triene ($C_3$-$C_{10}$) alpha olefin. The copolymer or terpolymer substrate has a molecular weight range of about 5,000 to about 500,000.

The disclosures in the foregoing patents and application which relate to VI improvers and fuel economizers for lubricating oils, namely U.S. Patents 3,933,656, 4,224,173 and 4,284,518; and U.S. Pat. Application Ser. No. 07/434,611 are incorporated herein by reference.

SUMMARY OF THE INVENTION

This invention provides a friction modifier for lubricants. The lubricating oil composition comprises a major amount of an oil of lubricating viscosity and a minor amount of a fuel economy additive prepared by the steps comprising:

(a) reacting a perfluoroaliphatic alcohol with a polyalkenyl alkenyl succinic acid anhydride in the presence of an acid catalyst to form a polyalkenyl succinic mono and/or diester mixture;

(b) heating the mixture to a temperature ranging from about 150° C. to about 180° C. for a period of about 2–4 hours to form the product of a polyalkenyl succinic mono and/or diester; and (c) recovering the product polyalkenyl succinic mono and/or diester.

DETAILED DESCRIPTION OF THE INVENTION

The present method of enhancing fuel economy in internal combustion engines is by chemically incorporating oligomeric perfluoroaliphatic alcohols onto a polyisobutylene polymer.

This method offers distinct advantages over other methods that utilize perfluorooligomers in lubricating oils. Firstly, polyisobutylene containing perfluorooligomers are completely soluble in a wide variety of solvents, including lubricating oils. This permits antifriction properties to be imparted to the lubricating oils in a wide variety of temperatures and engine operating conditions. Secondly, the methodology has application to polymers other than those with polyisobutylene backbones.

In practice of the process of this invention, the reagents are step wise reacted with a long chain hydrocarbyl substituted dicarboxylic acid anhydride containing residual unsaturation in a "one pot reaction". The long chain hydrocarbon group is a ($C_2$-$C_{10}$) polymer, e.g., a ($C_2$-$C_5$) monoolefin, the polymer having a number average molecular weight (Mn) of about 200 to about 10,000.

Preferred olefin polymers for reaction with the unsaturated dicarboxylic acid anhydride or ester are polymers comprising a major molar amount of ($C_2$-$C_O$) polymer, e.g., a ($C_2$-$C_5$) monoolefin. Such olefins include ethylene, propylene, butylene, isobutylene, pentene, I-octane, styrene, etc. The polymers can be homopolymers such as polyisobutylene, as well as copolymers of two or more of such olefins such as copolymers of: ethylene and propylene, butylene and isobutylene, propylene and isobutylene, etc. Other copolymers include those in which a minor molar amount of the copolymer monomers, e.g., 1 to 10 mole % is a ($C_4$-$C_{10}$) nonconjugateddolefin, e.g., a copolymer of isobutylene and butadiene; or a copolymer of ethylene, propylene and I,4-hexadiene; etc.

In some cases, the olefin polymer may be completely saturated, for example, an ethylene-propylene copolymer made by a Ziegler-Natta synthesis using hydrogen as a moderator to control molecular weight. In this case the alpha- or beta- unsaturated dicarboxylic acid anhydride is reacted with the saturated ethylenepropylene copolymer utilizing a radical initiator.

The long chain hydrocarbyl substituted dicarboxylic acid producing material, e.g., acid or anhydride used in the invention includes a long chain hydrocarbon, generally a polyolefin, substituted typically with an average of at least about 0.8 per mole of polyolefin, of an alpha- or beta- unsaturated ($C_4$-$C_{10}$) dicarboxylic acid, anhydride or ester thereof, such as fumaric acid, itaconic acid, maleic acid, maleic anhydride, chloromaleic acid, dimethylfumarate, chloromaleic anhydride, and mixtures thereof.

The alkenyl succinic acid anhydride may be characterized by the following formula

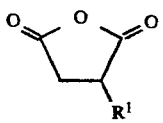

Where $R^1$ is polyisobutylene.

In the above formula, $R^1$ may be a residue (containing residual unsaturation) from a polyolefin which was reacted with maleic acid anhydride to for the alkenyl succinic acid anhydride. $R^1$ may have a number average molecular weight (Mn) ranging from about 200–10,000, preferably about 500–2,500, and more preferably from about 700–1,500.

Perfluoroaliphatic alcohols that can be used are those materials that contain the perfluoroaliphatic unit and are represented by the following formula

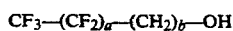

$$CF_3-(CF_2)_a-(CH_2)_b-OH$$

in Which the difluoro repeat unit, e.g., b, has a range of 1 to 20 and the hydrocarbon repeat unit, e.g., b, has a range of 2 to 10.

The perfluoroaliphatic alcohol may be a perfluoroaliphatic-1,1,2,2-tetra-H-ethyl alcohol having a molecular weight range of about 440 to about 525 and preferably an average molecular weight of about 475.

Examples of perfluoroaliphatic alcohols are those materials where the average perfluoroalkyl chain length is 7.3, or 8.2, or 9.0 while the hydrocarbon repeat unit may vary from 2 to 10, 2 being the preferred number. They are available commercially under the trademarks of Zonyl BA-L, Zonyl BA and Zonyl BA-N respective, and are available from E.I. Dupont deNemours and Co. of Wilmington, Delaware.

The formation of esters is enhanced by the presence of acid catalysts. One such catalyst is Amberlyst ®15 ion exchange resin (Reg. trademark of Rohm and Haas Co.). This strongly acidic, macroreticular resin is especially suitable for non-aqueous systems. An advantage of this particular catalyst is that it can be readily removed from the reaction product by filtration. These low-exchange resins have a polystyrene matrix cross-linked with 3-5% of divinylbenzene and they contain sulfonic acid groups.

The lubricating oil of the invention will contain the novel reaction product in a concentration ranging from about 0.1 to 10 wt.%. A preferred concentration range for the additive is from about 0.2 to 5 wt.% based on the total weight of the oil composition. A most preferred concentration range being from about 0.5 to 3.0 wt.%. Oil concentrates of the additives may contain from about 1 to 75 wt.% of the additive reaction product in a carrier or diluent oil of lubricating oil viscosity.

The novel reaction product of the invention may be employed in lubricant compositions together with conventional lubricant additives. Such additives may include dispersants, detergents, antioxidants, pour point depressants, anti-wear agents and the like.

The novel additive reaction product of the invention was tested for its effectiveness in conserving fuel in a fully formulated lubricating oil composition in the Sequence VI gasoline engine test.

The present additive is a mixture of mono and diesters represented by the following formulas:

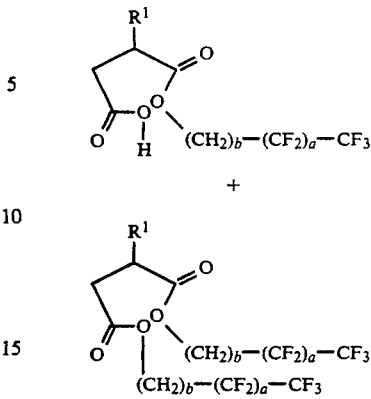

wherein the difluoro repeat unit, a, is 1–20 and the hydrocarbon repeat unit, b, is 2 to 10.

The following examples illustrate the preparation of the novel reaction product additive of this invention.

EXAMPLE I

Preparation of Alkenyl Succinic Mono- and/or Diester

A solution of polyisobutenylsuccinic acid anhydride (131.5 g, 0.1 moles, PIBSA prepared from an approximately 920 mol.wt. polybutene) in diluent oil (189.4 g) was charged into a 0.5 liter 3-neck flask equipped with a mechanical stirrer, thermometer, thermocouple and nitrogen inlet. Next, Zonyl BA (71.25 g, 0.15 moles) and Amberlyst I5 ion exchange resin (1.4 grams) was added and the heat was slowly increased to 180° C and maintained for 4.0 hours. The hot mixture ( 100° C) was filtered through diatomaceous earth filter aid. The product, a wax (an approximately 45 percent concentrates) analyzed as follows: Total Acid Number (TAN)=10.4.

EXAMPLE II

Preparation of Alkenyl Succinic Mono- and/or Diester

A solution of polyisobutenylsuccinic acid anhydride (131.5 g, 0.1 moles, pIBSA prepared from an approximately 920 mol.wt. polybutene) in diluent oil (189.4 g) was charged into a 0.5 liter 3-neck flask equipped with a mechanical stirrer, thermometer, thermocouple, and nitrogen inlet. Next Zonyl BA (71.25 g, 0.15 moles) an Amberlyst I5 ion exchange resin (1.4 for 4.0 grams) was added and the heat was slowly increased to 180° C and maintained for 4.0 hours. The hot mixture 100° C) was filtered through diatomaceous earth filter aid. The product, a wax (an approximately 45 percent concentrate), analyzed as follows: Total Acid Number (TAN)=16.6.

EXAMPLE III

Preparation of Alkenyl Succinic Mono- and/or Diester

A solution of polyisobutenylsuccinic acid anhydride (84.6 g. 0.2 moles, PIBSA prepared from an approximately 335 mol, wt. polybutene) in diluent oil (215.0 g) was charged into a 0.5 liter 3-neck flask equipped with a mechanical stirrer, thermometer, thermocouple, and nitrogen inlet. Next Zonyl BA (142.5 g. 0.3 moles) and Amberlyst 15 ion exchange resin (2.8 grams) was added and the heat was slowly increased to 180° C and maintained for 4.0 hours. The hot mixture was filtered through diatomaceous earth filter aid. The product a wax (an approximately 45% concentrate) analyzed as follows: Saponification Number 32.5.

EXAMPLE IV

Sequence VI Gasoline Engine Test Results

The ASTM Sequence VI dynamometer test can be used to qualify engine oils for the Energy Conserving Tier's I and II. The test uses a 1982 Buick 3.8 L V-6 engine equipped with an electrically controlled carburetor. The test compares candidate oils against ASTM's 20W-30 HR reference oil and measures the difference in brake specific fuel consumption (BSFC) that is, the engine's efficiency between the two oils. The Sequence VI test can detect difference in BSFC as small as 0.4 percent. The results are converted to an Equivalent Fuel Economy Index (EFEI) scale and reported as such. The higher the EFEI the greater the energy conserving properties of the formulation. Oil formulations containing the experimental additive were prepared without friction modifiers and tested, the results are shown below in Table I.

TABLE I

| Examples | Equivalent Fuel Economy Index (%)[a] |
|---|---|
| I | 1.84 |
| II | 3.12 |
| III | 2.39 |

[a] $1.70_{min}$ for Tier I and $2.70_{min}$ for Tier II

We claim:

1. A lubricating oil composition comprising a major amount of an oil of lubricating viscosity and a minor amount of a fuel economy additive prepared by the steps comprising:
   (a) reacting a perfluoroaliphatic alcohol with a polyalkenyl succinic acid anhydride in the presence of an acid catalyst to form a polyalkenyl succinic mono and/or diester mixture;
   (b) heating the mixture to a temperature ranging from about 150° C. to about 180° C. for a period of about 2-4 hours to form the product of an alkenyl succinic mono and/or diester; and
   (c) recovering the product polyalkenyl succinic mono and/or diester.

2. The lubricating oil composition of claim in which said polyalkenyl group has a number average molecular weight of about 200 to about 10,000.

3. The lubricating oil composition of claim 2 wherein said polyalkenyl group has a number average molecular weight of about 500 to about 2,500.

4. The lubricating oil composition of claim 1 wherein said perfluoroaliphatic alcohol is represented by the formula $$CF_3-(CF_2)_a-(CH_2)_bOH$$

in which the difluoro repeat unit, a, is 1-20 and the hydrocarbon repeat unit, b. is 2 to 10.

5. The lubricating oil composition of claim wherein said polyalkenyl group is polyisobutylene.

6. The lubricating oil composition of claim 2 wherein said polyalkenyl group has a number average molecular weight of about 700 to about 1500.

7. The lubricating oil composition of claim 1 wherein said acid catalyst is Amberlyst 15 ion exchange catalyst.

* * * * *